United States Patent
Long et al.

(10) Patent No.: US 9,147,334 B2
(45) Date of Patent: Sep. 29, 2015

(54) SYSTEM AND METHOD FOR MONITORING HOSPITAL WORKFLOW COMPLIANCE WITH A HAND HYGIENE NETWORK

(71) Applicant: Proventix Systems, Inc., Birmingham, AL (US)

(72) Inventors: Avery Dallas Long, Madison, AL (US); Harvey Allen Nix, Birmingham, AL (US); Feihong Xin, Birmingham, AL (US); Romeo Maurice Burtis, Birmingham, AL (US)

(73) Assignee: Proventix Systems, Inc., Birmingham, AL (US)

(*) Notice: Subject to any disclaimer, the term of this patent is extended or adjusted under 35 U.S.C. 154(b) by 0 days.

(21) Appl. No.: 14/024,300

(22) Filed: Sep. 11, 2013

(65) Prior Publication Data
US 2014/0009292 A1     Jan. 9, 2014

Related U.S. Application Data

(63) Continuation-in-part of application No. 13/736,945, filed on Jan. 9, 2013, which is a continuation-in-part of application No. 12/619,856, filed on Nov. 17, 2009, now Pat. No. 8,558,660, application No. 14/024,300,
(Continued)

(51) Int. Cl.
*G08B 21/00* (2006.01)
*G08B 21/24* (2006.01)
(Continued)

(52) U.S. Cl.
CPC ............ *G08B 21/245* (2013.01); *G06F 19/327* (2013.01); *G06Q 50/22* (2013.01); *H04Q 9/00* (2013.01); *H04Q 2209/47* (2013.01); *H04Q 2213/13095* (2013.01)

(58) Field of Classification Search
None
See application file for complete search history.

(56) References Cited

U.S. PATENT DOCUMENTS

| 5,363,425 A | 11/1994 | Mufti et al. |
| 5,572,195 A | 11/1996 | Heller et al. |

(Continued)

FOREIGN PATENT DOCUMENTS

| KR | 1020030056886 | 7/2003 |
| KR | 1020030064068 | 7/2003 |

OTHER PUBLICATIONS

Lindqvist, "RFID Monitoring of Health Care Routines and Processes in Hospital Environment", Master's Thesis, Aug. 10, 2006; p. 73: 5.2.1 Modular Design; Helsinki University of Technology, Department of Electrical and Communications Engineering.
(Continued)

*Primary Examiner* — Firmin Backer
*Assistant Examiner* — Brian Wilson
(74) *Attorney, Agent, or Firm* — Edward H Kiessling, IV

(57) ABSTRACT

A system and method for monitoring compliance with a plurality of workflow procedures in a hospital or other health care facility using a hand hygiene compliance system (HHC). A control unit of an HHC gathers data based upon the presence, identification, and movement of a plurality of assets, including persons, equipment, or supplies, each having wearable detectable tags, such as RFID tags, and communicates that data to a local or remote server. The server is programmed to monitor or cause compliance with hospital workflow procedures relevant to the communicated data, such as rounding requirements and proper use of equipment, or may generate alarms or notifications where a workflow procedure has not been followed.

24 Claims, 9 Drawing Sheets

Related U.S. Application Data which is a continuation-in-part of application No. PCT/US2012/052901, filed on Aug. 29, 2012, and a continuation-in-part of application No. 13/149,283, filed on May 31, 2011, now abandoned.

(60) Provisional application No. 61/116,057, filed on Nov. 19, 2008, provisional application No. 61/575,848, filed on Aug. 30, 2011.

(51) Int. Cl.
  *H04Q 9/00* (2006.01)
  *G06Q 50/22* (2012.01)
  *G06F 19/00* (2011.01)

(56) References Cited

U.S. PATENT DOCUMENTS

| | | | |
|---|---|---|---|
| 5,793,653 A | 8/1998 | Segal | |
| 5,945,910 A | 8/1999 | Gorra | |
| 6,150,948 A | 11/2000 | Watkins | |
| 6,154,139 A | 11/2000 | Heller | |
| 6,236,317 B1 | 5/2001 | Cohen et al. | |
| 6,392,546 B1 | 5/2002 | Smith | |
| 6,426,701 B1 | 7/2002 | Levy et al. | |
| 6,577,240 B2 | 6/2003 | Armstrong | |
| 6,727,818 B1 * | 4/2004 | Wildman et al. | 340/573.1 |
| 6,876,303 B2 | 4/2005 | Reeder et al. | |
| 6,882,278 B2 | 4/2005 | Winings et al. | |
| 7,015,816 B2 | 3/2006 | Wildman et al. | |
| 7,116,230 B2 | 10/2006 | Klowak | |
| 7,242,307 B1 | 7/2007 | LeBlond et al. | |
| 7,277,889 B2 | 10/2007 | Addonisio et al. | |
| 7,375,640 B1 | 5/2008 | Plost | |
| 7,408,470 B2 | 8/2008 | Wildman et al. | |
| 7,457,765 B2 * | 11/2008 | Thompson et al. | 705/7.14 |
| 7,466,232 B2 | 12/2008 | Neuwirth | |
| 7,518,502 B2 | 4/2009 | Austin et al. | |
| 7,551,092 B1 | 6/2009 | Henry | |
| 7,605,704 B2 | 10/2009 | Munro et al. | |
| 7,652,576 B1 | 1/2010 | Crossno et al. | |
| 7,734,476 B2 | 6/2010 | Wildman et al. | |
| 7,782,214 B1 | 8/2010 | Lynn | |
| 7,801,506 B2 | 9/2010 | Haave et al. | |
| 7,804,409 B2 | 9/2010 | Munro et al. | |
| 7,855,651 B2 | 12/2010 | LeBlond et al. | |
| 7,898,407 B2 | 3/2011 | Hufton et al. | |
| 7,952,484 B2 | 5/2011 | Lynn | |
| 8,045,498 B2 | 10/2011 | Hyland | |
| 8,169,327 B2 | 5/2012 | Lynn | |
| 2002/0135486 A1 | 9/2002 | Brohagen et al. | |
| 2003/0052788 A1 | 3/2003 | Kwong-Tai Chung | |
| 2004/0150527 A1 | 8/2004 | Harper et al. | |
| 2006/0267731 A1 * | 11/2006 | Chen | 340/10.1 |
| 2007/0028119 A1 | 2/2007 | Mirho | |
| 2007/0080801 A1 | 4/2007 | Weismiller et al. | |
| 2007/0096930 A1 | 5/2007 | Cardoso | |
| 2007/0210923 A1 | 9/2007 | Butler et al. | |
| 2007/0229288 A1 | 10/2007 | Ogrin et al. | |
| 2007/0257803 A1 | 11/2007 | Munro et al. | |
| 2007/0285229 A1 | 12/2007 | Batra et al. | |
| 2007/0285241 A1 | 12/2007 | Griebenow et al. | |
| 2008/0001763 A1 | 1/2008 | Raja et al. | |
| 2008/0106374 A1 | 5/2008 | Sharbaugh | |
| 2008/0131332 A1 | 6/2008 | Nguyen et al. | |
| 2009/0018882 A1 | 1/2009 | Burton et al. | |
| 2009/0091458 A1 | 4/2009 | Deutsch | |
| 2009/0171695 A1 | 7/2009 | Cobbinah et al. | |
| 2009/0184823 A1 * | 7/2009 | Tessier | 340/568.1 |
| 2009/0195385 A1 | 8/2009 | Huang et al. | |
| 2009/0219131 A1 | 9/2009 | Barnett et al. | |
| 2009/0224907 A1 | 9/2009 | Sinha et al. | |
| 2009/0273477 A1 | 11/2009 | Barnhill | |
| 2009/0295539 A1 | 12/2009 | Mahmoodi et al. | |
| 2009/0299787 A1 | 12/2009 | Barnhill | |
| 2010/0117836 A1 | 5/2010 | Seyed Momen et al. | |
| 2010/0134296 A1 | 6/2010 | Hwang | |
| 2010/0156599 A1 | 6/2010 | Ainsbury et al. | |
| 2010/0164728 A1 | 7/2010 | Plost | |
| 2010/0256983 A1 | 10/2010 | Perkins | |
| 2010/0265059 A1 | 10/2010 | Melker et al. | |
| 2010/0315243 A1 | 12/2010 | Tokhtuev et al. | |
| 2010/0328076 A1 | 12/2010 | Kyle et al. | |
| 2011/0019205 A1 | 1/2011 | Gerber et al. | |
| 2011/0046921 A1 | 2/2011 | Sahud | |
| 2011/0093313 A1 | 4/2011 | LeBlond et al. | |
| 2011/0153349 A1 | 6/2011 | Anderson et al. | |
| 2011/0169645 A1 | 7/2011 | Cartner et al. | |
| 2011/0169646 A1 | 7/2011 | Raichman et al. | |
| 2011/0254682 A1 | 10/2011 | Sigrist Christensen | |
| 2012/0154582 A1 | 6/2012 | Johnson et al. | |

OTHER PUBLICATIONS

Yaó, "The Use of RFID in Healthcare: Benefits and Barriers", Retrieved from the Internet: http://www.personal/psu.edu/wxy119/pub/FRID-TA-210-WEN-final.pdf, Jan. 31, 2010.

Sharir, R et al., "High-level handwashing compliance in a community teaching hospital: a challenge that can be met." The Hospital Infection Society, 2001.

Boyce, John M. MD, et al., "Guideline for hand hygiene in healthcare settings", From the Hospital of Saint Raphaeal, New Haven and University of Geneva, 2002.

Lankkford, Mary G. et al., "Influence of Role Models and Hospital Design on Hand Hygiene of Health Care Workers", Emerging Infections Diseases, Feb. 2003, pp. 217-223, vol. 9, No. 2.

New Mexico MRSA Collaborative, "Employee Observations, Observation Instructions for Isolation Patients".

Larson, Elaine L., RN, PhD, FAAN, CIC, "APIC Guidelines for Infection Control Practice", 1992, 1993, and 1994 APIC Guidelines Committee, Association for Professionals in Infection Control and Epidemiology, Inc.

Michigan IT Companies Helping the University of Miami Center for Patient Safety Tackle a Leading Cause of Death Using an RTLS Solution to Monitor Staff Hand-Washing Compliance,"Jul. 29, 2009, accessible at http"//news.bio-medicine.org/, printed May 9, 2013.

* cited by examiner

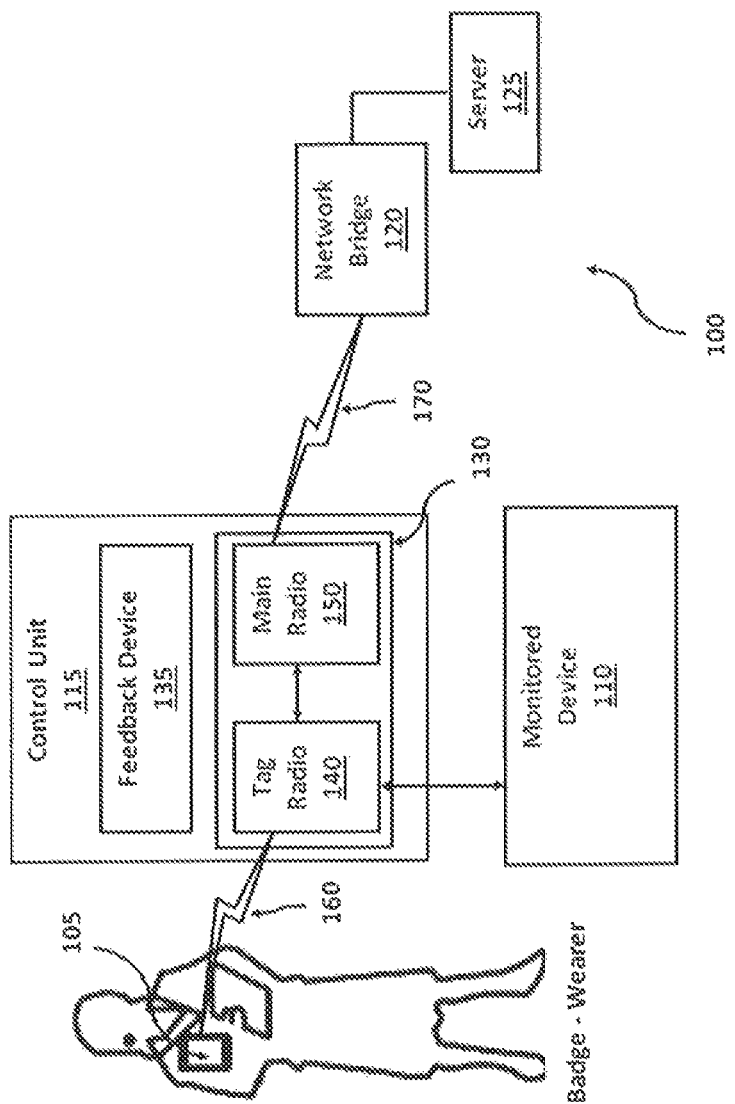

SYSTEM AND METHOD FOR MONITORING HOSPITAL WORKFLOW COMPLIANCE WITH A HAND HYGIENE NETWORK

CROSS REFERENCE TO RELATED APPLICATIONS

This application is a continuation-in-part of, and claims the benefit of and priority to, each of the following applications: U.S. application Ser. No. 13/149,283 filed on May 31, 2011; U.S. application Ser. No. 12/619,856 filed on Nov. 17, 2009, which claims priority to U.S. Provisional Application No. 61/116,057 filed on Nov. 19, 2008; U.S. application Ser. No. 13/736,945 filed on Jan. 9, 2013, which is a continuation-in-part of and claims the benefit of and priority to U.S. application Ser. No. 12/619,856; and PCT Application Ser. No. PCT/US2012/052901 filed on Aug. 29, 2012, which claims priority to U.S. Provisional Application No. 61/575,848.

TECHNICAL FIELD

The present invention relates to the use of a communications network created by a hand hygiene compliance (HHC) system in conjunction with a plurality of wearable tags on hospital personnel and other assets to monitor or cause compliance with hospital workflow procedures.

BACKGROUND

The issue of hospital acquired infections is well known within and outside the health care community. Such infections kill more Americans each year than AIDS, breast cancer, and automobile accidents combined. To date many studies have been conducted in an effort to ascertain effective ways to reduce the occurrence of such infections, and the clear majority finds a thorough cleansing of one's hands prior to treating a patient as the single most important way to protect against the spread of hospital-acquired infections, As a result, many hospitals have implemented HHC systems for purposes of monitoring whether such persons wash their hands upon entering a patient's room. As such, HHC systems monitoring hand hygiene compliance are well established in the prior art.

However, the communication networks created by the aforementioned HHC systems generally monitor and report only hygiene-related events. As a result, these communication networks do not monitor non-hygiene events associated with a piece of equipment (i.e., a catheter), a supply, or a person for purposes of providing information relevant to hospital procedures, such as workflow procedures, based on data related to the piece of equipment, the supply, or the person. If HHC systems were improved to provide such non-hygiene related information, patient care would increase due to an increase in compliance with hospital workflow procedures which would result in an even greater overall reduction in the number of hospital-acquired infections. While current HHC systems are effective in monitoring hand hygiene compliance, they do not monitor and provide information related to various non-hygiene events (i.e. hospital workflow procedures).

Further, healthcare facilities routinely seek systems capable of monitoring and identifying tagged assets (that is, hospital employees having a wearable tag) use of hand hygiene dispensers. While wireless communications systems attempt to meet this need, they are subject to inefficiencies in terms of detecting and identifying, in a uniform manner, tagged assets' proximity to and use of a monitored device. Within the context of wireless communications, it is well known that transmitting data wirelessly poses significant challenges which must be addressed before robust and reliable communications may be achieved. One challenge, which is relevant to the present disclosure, relates to the noticeable decrease in system accuracy resulting from assigning both short range and long range communications functions to an individual node or connection point in the wireless communications system.

As an example of the challenge mentioned above, current wireless communications systems employing Radio Frequency Identification (RFID) technology require a single RF radio of a microcontroller not only detect use of a monitored device by a tagged asset but also relay data relating to use of the monitored device to a server. This amounts to the RF radio handling both short range communications (that is, communications broadcast by tagged assets in proximity to the monitored device) as well as long range communications involving the server. With system resources available to a RF radio already limited by its RF engine, the RF radio cannot detect a short range communication from a tagged asset using the monitored device while simultaneously transmitting a long range communication to the server. Accordingly, results relating to use of a monitored device may not represent an accurate measure of the frequency with which the device is used. Furthermore, since the RF radio, tagged assets, and server are confined to communicating on the same channel of the network, the accuracy of results relating to use will decrease as the number of tagged assets increase due to an increase in the probability of the RF radio missing short range communications from tagged assets.

Another challenge, which stems from having a single RF radio handle short and long range communications, concerns power consumption of wearable RFID tags affixed to tagged assets. Having one RF radio per monitored device means RFID tags must listen for network traffic prior to communicating with the RF radio to avoid data collisions. This causes RFID tags to stay on longer, consuming more power per communication, which over time reduces the battery life of the wearable RFID tags. Therefore, there is a need for a wireless communications system employing RFID technology which overcomes these shortcomings.

SUMMARY

Embodiments of the present invention provide a system for monitoring compliance with a plurality of workflow procedures in a hospital or other health care facility using an HHC system. The system includes a HHC system, which provides a communications network capable of detecting the presence of a hospital employee having a wearable tag, preferably in the form of a RFID tag, and monitoring whether the hospital employee washed his hands upon entering a patient's room. Each HHC control unit (that is, a hand washing station equipped with a sensor and communication devices) is provided with a feedback device in the form of a small display and necessary hardware to communicate with the wearable tag and a communications network, such as a wireless computer network. Through the communications network, the control unit is in communication with computing devices throughout the hospital, including, for example, servers or personal computers at an administrator's desk or nurses' stations. The display associated with each server or computer associated with the communication network operates as a feedback device in embodiments of the present invention.

In one embodiment, the control units gather data based upon the presence, identification, and movement of a plurality of assets having the wearable tags, and communicating that data to a local or remote server. The assets monitored by the HHC system may be persons, equipment, or supplies. The server is programmed to monitor or cause compliance with hospital workflow procedures. For example, the system may generate a report of compliance with hospital procedure from data gathered by the HHC system in response to a query by a user and display the report of compliance on a feedback device located in the hospital. One such report may include a hospital rounding report based upon the movement of hospital personnel (i.e. nurses, doctors, security guards) equipped with RFID tags, into rooms equipped with a HHC system. The system also may automatically select one or more hospital procedures relevant to the content of data gathered by the HHC and provide workflow instruction through a feedback device to a person performing such procedure to ensure compliance with the procedure. For example, a control unit may detect the presence of an RFID-tagged piece of equipment, such as a catheter, in a room, and in response to movement of the catheter by a RFID-tagged nurse, display a procedure on a feedback device associated with the control unit relating to proper administration of the catheter and further requiring input confirming compliance with the procedure by the nurse. The system also may automatically generate an alarm or notification signifying a procedure is not currently being followed, in response to data gathered by the HHC. For example, the system may dynamically update patient rounding status, including based upon rounding intervals specific to individual patents based upon their health status, and in a preferred embodiment display a red screen or audible warning on a feedback device at a nurses' workstation when the maximum time between visits to a patient's room has elapsed.

These and other embodiments of the present invention will become readily apparent to those skilled in the art from the following detailed description of the embodiments having reference to the attached figures, the invention not being limited to any particular embodiment(s) disclosed.

BRIEF DESCRIPTION OF THE DRAWINGS

FIG. 1 is a schematic of one embodiment of a system for detecting and identifying device utilization

DETAILED DESCRIPTION

Figure 1A:
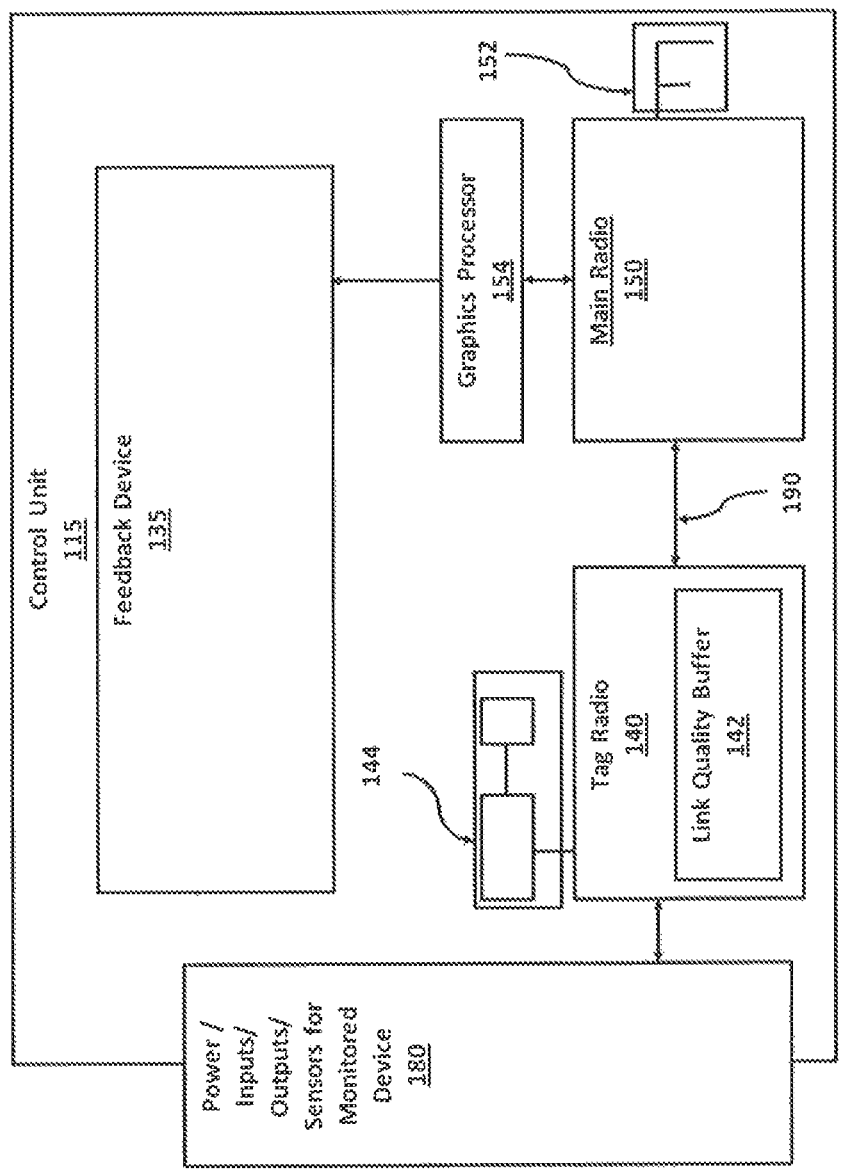
FIG. 1A is a detailed schematic of the control unit shown in FIG. 1.

The various embodiments of the present invention and their advantages may be understood by referring to FIGS. 1 through 6 of the drawings. The elements of the drawings are not necessarily to scale, emphasis instead being placed upon illustrating the principles of preferred embodiments of the present invention. Throughout the drawings, like numerals are used for like and corresponding parts of the various drawings. This invention may be provided in other specific forms and embodiments without departing from the essential characteristics as described herein. The embodiments described below are to be considered in all aspects as illustrative only and not restrictive in any manner.

The present invention relates to a system comprising hand hygiene compliance (HHC) system comprising a plurality of control units, a plurality of wearable tags, and a server. The wearable tags, which in a preferred embodiment are in the form of a plurality of RFID tags, are associated with an asset consisting of a person, a piece of equipment, and a supply. The control units are operable to detect and identify wearable tags within a predetermined proximity of the control units and communicate data over a communications network associated with the system to the server. Upon receiving the data, the server is operable at least in part on the data to perform at least one of the following actions: generate a report of compliance with a hospital procedure in response to a query by a user and display the report of compliance on a feedback device; select at least one hospital procedure relevant to the data and provide workflow instructions to a person performing such procedure; or generate a notification regarding compliance with a hospital procedure.

As used herein, the term "server" broadly refers to any computing device with a processor programmed to perform the functions described herein, and may include without limitation traditional servers, desktop or notebook computers, tablets, smart phones or PDAs, and any like device now existing or hereinafter developed. Likewise, the term "feedback" device broadly refers to any visual, auditory, or tactile device capable of conveying information to a person, including displays associated with HHC control units or displays of servers (as previously defined), or displays of workstation or client computers or devices receiving reports or other information from servers to convey to relevant healthcare providers. Further, the basic components and operation of an HHC system are known to those of ordinary skill in the art and will not be described in detail here.

FIG. 1 depicts one embodiment of a hand hygiene compliance system (100) comprising a wearable tag (105), a control unit (115), a network bridge (120), and a server (125). The wearable tag (105) is preferably an RFID badge worn by a healthcare employee. The control unit (115) is associated with a monitored device (110), such as a hand hygiene dispenser, and further includes a plurality of microcontrollers (130) with integrated RF transceivers, and a feedback device (135). More specifically, one of the microcontrollers (130), hereinafter referred to as a tag radio (140), detects short-range wireless transmissions (160) from the wearable tag (105) when it is within a predetermined proximity of the control unit (115). Likewise, a second microcontroller (130), hereinafter referred to as the main radio (150), processes long-range wireless transmissions (170) involving the network bridge (120) or server (125). Furthermore, the tag radio (140) and the main radio (150) communicate on separate channels of a wireless network.

The control unit (115) may be provided with sensors, such as capacitive sensors, infrared sensors, vibration sensors, or other devices suitable for detecting when an individual is in proximity to the monitored device (110) or has physically contacted the monitored device (110). Further, the feedback device (135), which is a display screen associated with the control unit (115), may display selected content to an individual using the monitored device (115) upon detection of a parameter indicating use. of the device (115). For example, selected content may include a touch-screen or touch-free menu of icons that allow an individual to, without limitation, communicate, enter, obtain, or update workflow information through the selection of one or more icons.

Figure 1B:
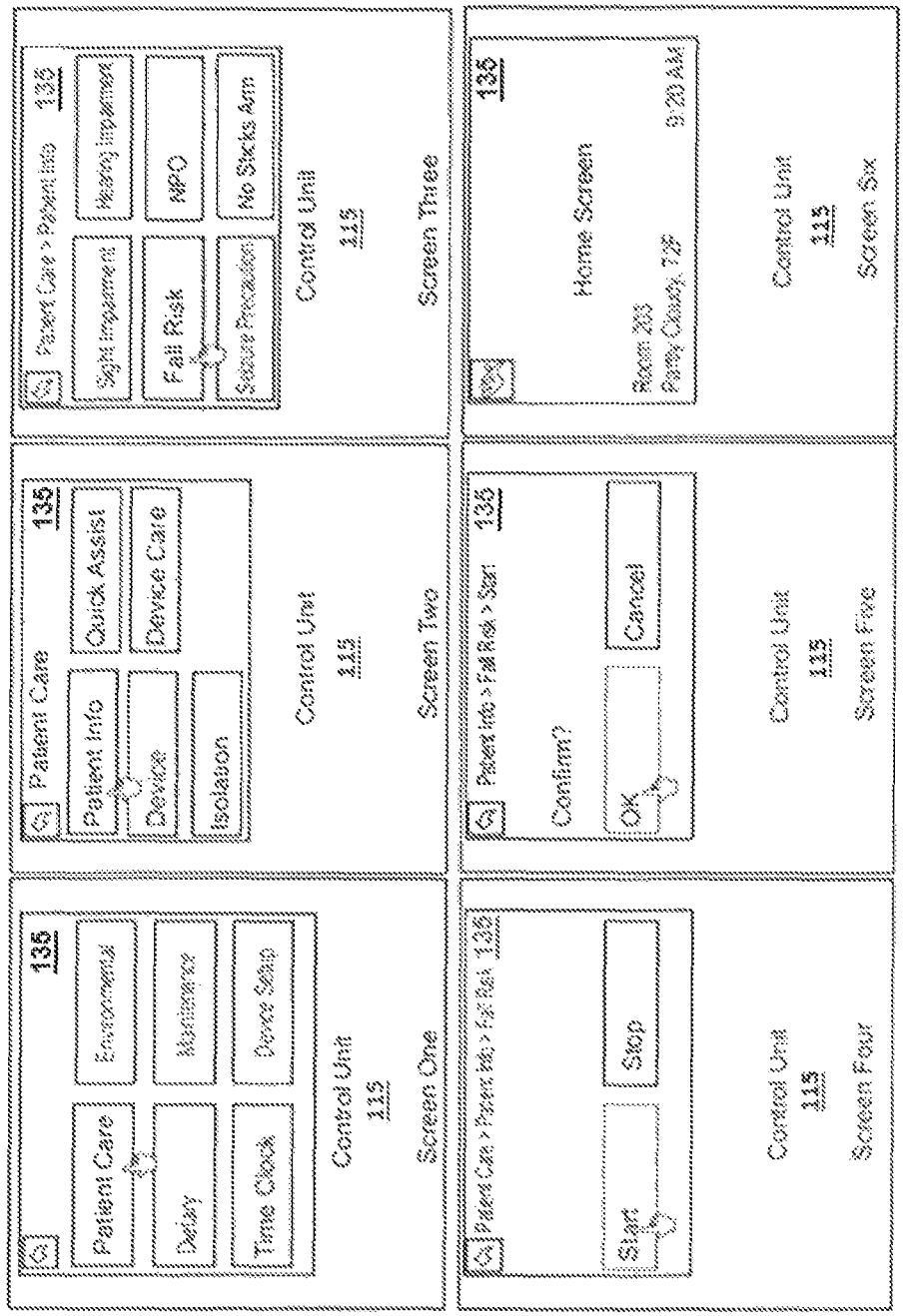
FIG. 1B depicts workflow information being updated via the selection of a sequence of icons on a touch-screen menu displayed on the feedback device shown in FIG. 1.

As shown in FIG. 1B, healthcare workers can enter or update workflow information (that is, enter new patient condition information or update existing patient condition information) via a touch-screen menu displayed on the feedback device (135). More specifically, after using a hand hygiene dispenser associated with the control unit (115), a healthcare worker can update existing patient care information to classify a patient as a fall risk through the selection of one or more icons on the touch-screen menu. Once the healthcare worker finishes selecting icons, a fall risk icon will be displayed on the feedback device (135) until a healthcare worker or other authorized personnel indicates the patient is no longer a fall risk.

The selected content may be transmitted from the server (125), control unit (115), or other sources under the control of the server (25) or control unit (115). Further, the content or material displayed on the feedback device (135) may be determined based upon the identity of the user associated with a particular tag (105), the identity of a patient resident in a room or area, the device (110), or any combination thereof. As an example, a physician, nurse or therapist seeing a patient for a certain condition or illness may wish to view one or more of a patient's vital signs (e.g. blood pressure or heart rate) or other patient-specific. information before initiating contact with or treatment of the patient. A physician may wish to have different information than a nurse or therapist regarding the patient. For example, a physician may wish to see only information relevant to a condition for which the patient is being treated. For example, a cardiologist may wish to see different patient-specific information than an internist treating a patient for a different condition. Thus, selected content may be specific to the patient and/or the specific health care provider. In addition, selected content may also include compliance information for a particular individual or an average compliance for all users, providing motivation for compliance with procedures.

Referring now to FIGS. 1 and 1A in conjunction, the tag radio (140) includes a patch antenna (144) as well as a link quality buffer (142). As such, via the patch antenna (144), the tag radio (140) detects, over a first communications channel, short-range wireless communications (160) from a wearable tag (105) that is within a predetermined proximity of the control unit (115). In one embodiment, the tag radio (140) has a room entry/exit threshold which allows the tag radio (140) to detect a wearable tag (105) worn by a hospital employee or other similar personnel entering or exiting a room or area in which a monitored device, such as a hand hygiene dispenser, is located. As follows, the tag radio (140), via the patch antenna (144), detects a short-range wireless transmission (160) from at least one wearable tag (105) entering a room or area in which the control unit (115) is located. Further, upon receiving the short-range wireless transmission (160), the tag radio (140) analyzes a Radio Signal Strength Indicator (RSSI) value associated with the transmission (160) and, based upon the RSSI value, makes one of two associations If the RSSI value associated with the short-range transmission (160) equals or exceeds a predetermined threshold value (that is, the room entry/exit threshold), then the tag radio (140) stores, in the link quality buffer (142), a unique identification code assigned to the tag (105). The tag radio (140) continues to store the identification code in the buffer (142) until the tag radio (140) receives a predetermined number of short-range wireless transmissions (160) from the tag (105) that are below the predetermined threshold value. When this occurs, the tag radio (140) deduces the tag (105) is no longer present in the room or area, and removes the identification code from the buffer (142). Otherwise, if the transmission (160) is below the threshold value, and the identification code is not already present in the buffer (142), then the tag radio (140) ignores the transmission because the tag (105) has not, at this time, entered the room or area in which the control unit (115) is located.

Further, using the RSSI value associated with each short-range wireless transmission (160), the tag radio (140) may detect other events, such as the identity of a healthcare employee who is within a predetermined proximity (e.g. a wash zone) of a hand hygiene dispenser when a control unit (115) associated with the dispenser detects a parameter indicating use thereof. Therefore, by analyzing the RSSI value associated with each short-range wireless transmission (160), the tag radio (140) can determine not only whether a wearable tag is in a room or area in which the control unit (115) is located, but also whether the tag (105) is near a monitored device (110), such as a hand hygiene dispenser, when the control unit (115) detects use thereof.

In addition to measuring the RSSI value associated with a short-range wireless transmission from a wearable tag (105), the tag radio (140) communicates data to the main radio (150) via a wired communication (190), wherein data relates to at least at the unique identification code assigned to the tag (105). As follows, upon receiving the data, the main radio (150) uses a planar inverted F (PIF) antenna to send data to either the network bridge (120) or the server (125) via a long range wireless transmission (170) that occurs over a second communications channel.

Referring now to FIG. 1, a plan view of a hospital floor equipped with the hand hygiene compliance system is depicted having a plurality of rooms, shown generally as (200), (201), (202), and (203). A nurse (210) having a wearable tag (105) is shown performing patient rounding by entering and exiting room (200), room (201), and room (203). In this particular embodiment, a plurality of control units (130) detect movement of the nurse (210) in each of the aforementioned rooms by way of a short-range wireless transmission (160) occurring between the wearable tag (105) and the tag radio (140) associated with each of the control units (130). The short-range wireless transmission (160) occurs when the wearable tag (105) associated with the nurse (210) enters a predetermined proximity of the control unit (130). As follows, in this illustrative embodiment, the wearable tag (105) enters the predetermined proximity upon the nurse (210) entering room (201), room (202), and room (203) and triggers the occurrence of the short-range wireless transmission (160).

Still referring to FIG. 1, the control units (115) obtain, via the short-range wireless transmission (160), data relating to location, movement, time of detection, signal strength, and identity of the wearable tag (105) worn by the nurse (210) and subsequently transfers the data to the server (125) via the PIF antenna (152) of the main radio (150). As will be discussed in detail in subsequent FIG. 2, in one embodiment, the server (125) in response to a query by a user is operable to generate a report of compliance with a hospital procedure based at least in part on data received from the short-range wireless transmission (160) and further displays the report of compliance on a feedback device (230). For example, as shown generally in FIG. 2, a nurse (210), upon completing patient rounding, enters a nurses' work station (220) for purposes of consulting the feedback device (230) for a report of compliance with a hospital procedure relating to patient rounding. However, while this particular embodiment illustrates the feedback device (230) located at a nurses' work station (220), the feedback device (230) may be located at other locations of the hospital floor such as an administrator's desk, or remotely in connection with any server or computing device in communication with the hospital's information systems via a local or wide-area communications network, including the internet.

Figure 3:
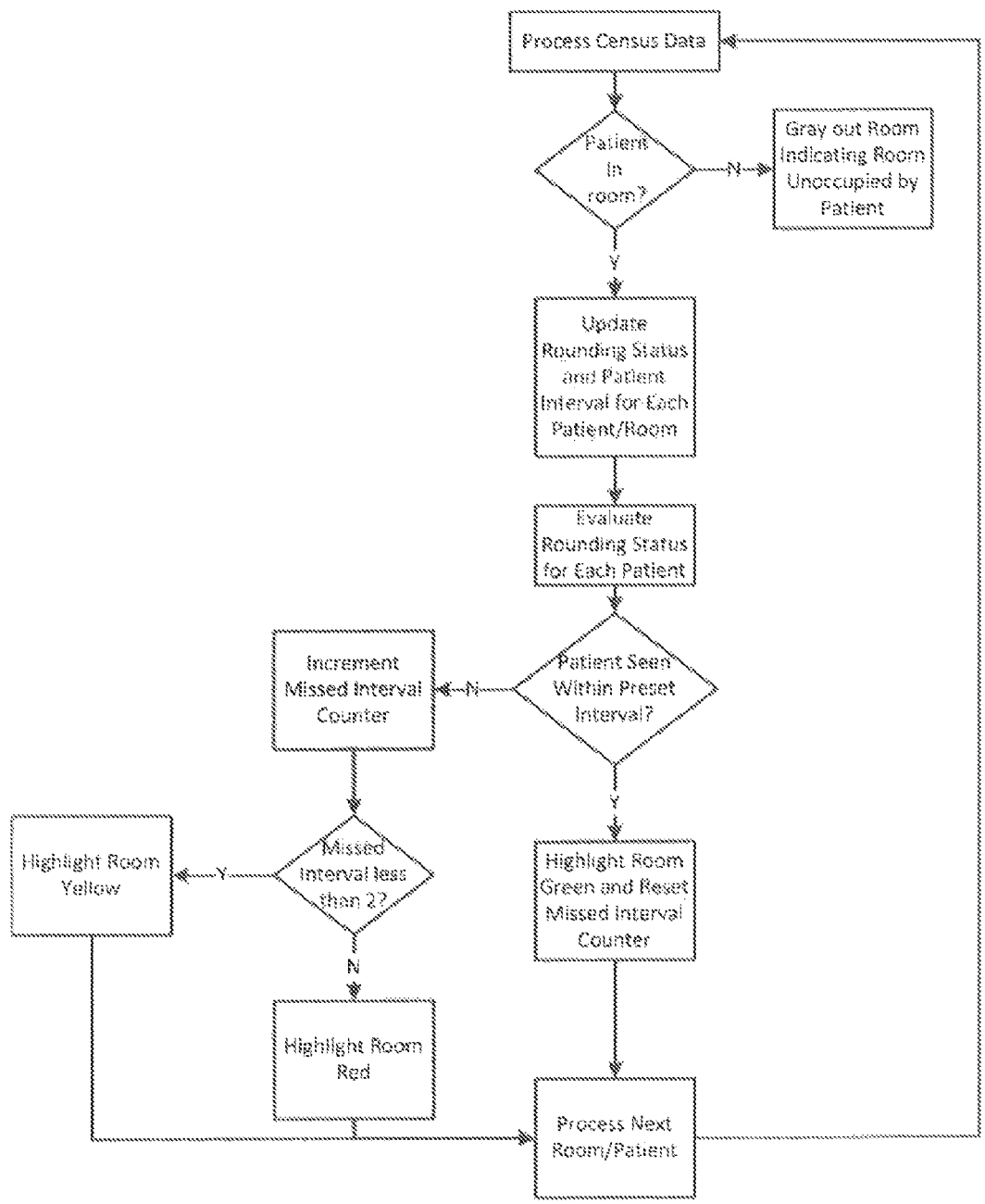
FIG. 3 is a flowchart illustrating one embodiment of a process of using data gathered by a HHC system to generate an automated rounding report.

Turning to FIG. 3, a flowchart of one embodiment is provided depicting processes the server (125) performs while generating a report of compliance with a hospital procedure. In this flowchart, the processes the server performs relate to generating an automated rounding report for a plurality of patients in a hospital, with the automated rounding report subsequently depicted in FIG. 6. When generating the automated rounding report, the server (125) begins by accessing an admit discharge transfer (ADT) Census database, which allows the server (125) to ascertain a timestamp indicating when a patient was admitted and a timestamp indicating when a patient was discharged. Furthermore, the ADT Census database also tells the server a location (i.e. a room number) of a patient assuming the patient has not been discharged. After acquiring these parameters, the server logically matches each of a plurality of rooms on a floor of a hospital with each of the patients contained in the ADT Census database. However, in the event the ADT Census database contains no record of a patient being admitted to a room on a floor in the hospital, the server (125) designates the room as unoccupied, for example by displaying the room as a particular color (e.g., white) in the automated rounding report. The server (125) regularly monitors the ADT Census database, so the automated rounding report generated remains dynamic and false alarms are not generated based Upon a patient who has been discharged from his or her room.

Referring still to FIG. 3, the server (125) next performs a status check for each of the patients by accessing a patient information database. The status check provides health condition data of each of the patients, for example whether the patients are in good, fair, or critical condition, or other indicia adopted by a particular hospital, department, or floor, as indicated by corresponding records in the patient information database. A rounding interval is assigned for each of the patients based upon the health condition data gathered from the records of the patient information database. The rounding interval may vary depending on this information. Generally, a hospital's procedures relating to patient rounding requires a member of hospital personnel to visit each of the patients on an hourly basis. However, a hospital's procedures may require more frequent visits by hospital personnel in the event heightened care is required. In addition, in a preferred embodiment, an authorized user may override the rounding interval assigned to assign a more specific rounding interval for a given patient.

Figure 2:
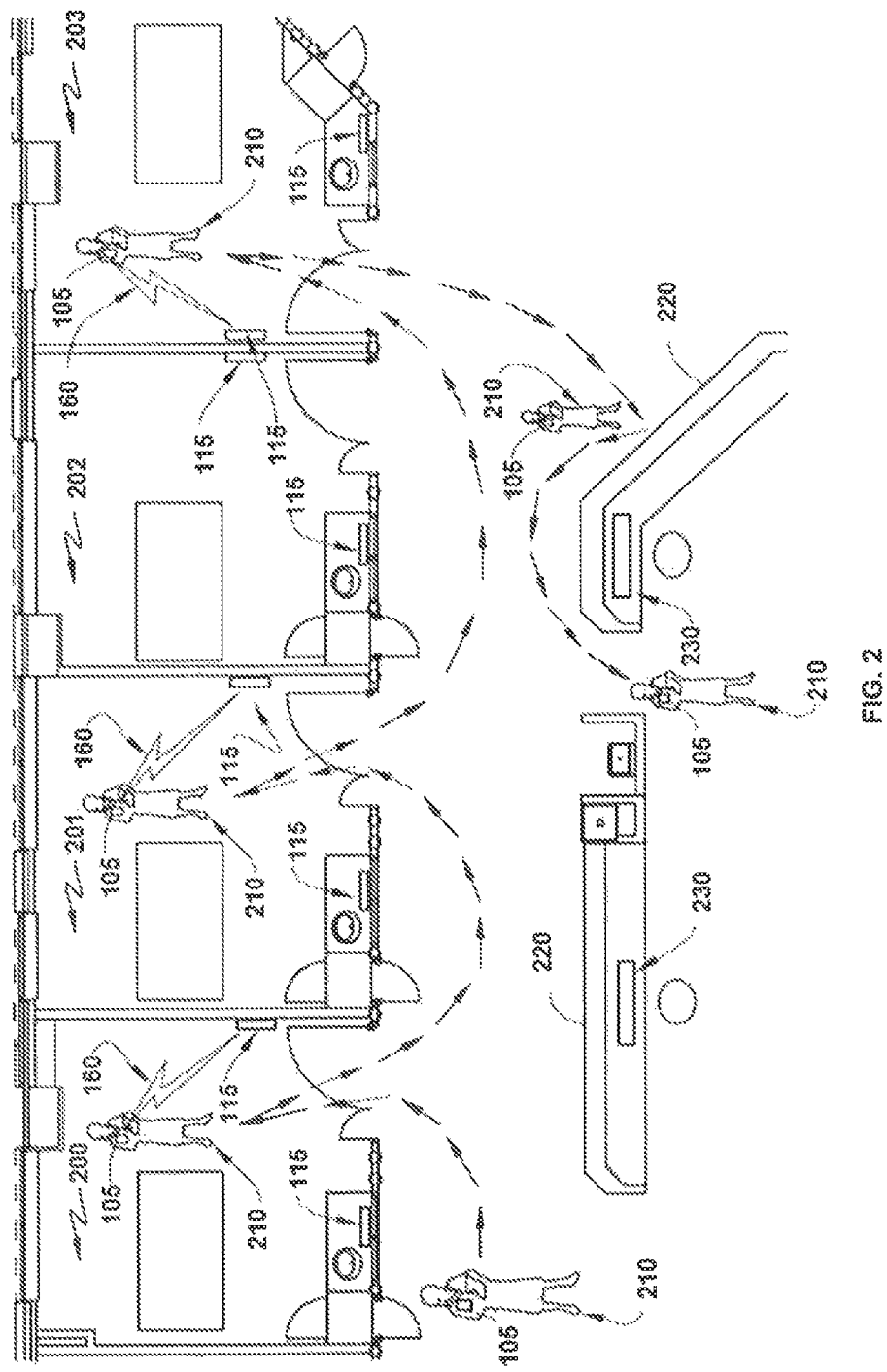
FIG. 2 depicts an exemplary plan view of a hospital floor equipped with an HHC system tracking movement of a nurse having a wearable tag performing patient rounding.

Referring now to FIG. 3 in conjunction with FIGS. 1 and 2, after a rounding interval for each of the patients contained in the ADT Census database has been assigned, the server accesses data received from the control units (115) located in each of the rooms occupied by each of the patients. Then the server (125) analyzes the data to ascertain a rounding status for each of the patients. Using FIG. 2 as an example, the rounding status tells the server (125) how long it has been since the nurse (210) having the wearable tag (105) entered each of the rooms occupied by each of the patients, based upon the time of detection of the wearable tag (105) by the control units (115). In FIG. 2, the rounding status for room (200), room (201), and room (203) would depict the nurse (210) as having been the last wearable tag (105) to visit. However, room (202) may have a rounding status separate and distinct from room (200), room (201), and room (203) since the nurse (210) did not enter room (202) while performing patient rounding.

Once the server (125) determines a rounding status for each of the patients, the server compares the rounding status for each of the patients against the rounding interval for each of the patients and assigns a corresponding compliance indicator to each patient. The compliance indicator, as its name suggests, is a cue communicating the extent to which the patient's rounding status is in compliance with hospital procedure. The compliance indicator may be a numeric value (such as a range from 1 to 10), a "star" system (such as 1 to 5 stars), a color range (green, yellow, red), or any other similar system for conveying information, The compliance indicator may also utilize sound, such as a beep of varying frequency or interval based upon the rounding status of the reported patients. In a preferred embodiment, a color system is used, with a color block corresponding to each room, as such a format can be seen and understood from a distance, without having to read any text. Further, in a still preferred embodiment, a compliance factor for various levels of compliance or noncompliance may be assigned and adjusted. The compliance factor controls the state change of the compliance indicator with respect the extent of compliance with the hospital procedure. The compliance indicator may be binary (compliant or non-compliant), or it may have three or more states (complaint, varying degrees of non-compliance, urgent non-compliance). In the case of rounding, a particular department may have defined the compliance indicator as green ("compliant), yellow ("nearing non-compliant" or "moderately non-compliant"), and red ("urgent non-compliance"). The department may wish the compliance indicator to change from "compliant" (e.g., green) to "nearing non-compliant" (e.g., yellow) when the rounding interval is 90% complete (e.g., for one-hour, rounding interval, 54 minutes since the last round by a nurse), and change from "nearing non-compliant" to "non-compliant" (e.g., "red") when 110% of the rounding interval has elapsed without visitation. An auditory alarm may be added as yet another threshold is passed. Such compliance indicia and compliance factors may be selected by the hospital staff based upon patient health status, departmental practice, physician orders, customary standard of care, or any combination thereof Referring to FIGS. 1, 2 and FIG. 3 again as an example, assuming room (202) had a rounding interval of one hour, the server, after determining the rounding status for room (202), would determine whether the nurse (210) having the wearable tag (105) had visited room (202) within the past hour. As such, if the rounding status depicted the nurse (210) having the wearable tag (105) entering room (202) within the past hour, the server (125) shall be prompted to assign a compliance indicator of green to room (202) depicted in the automated rounding report. If the rounding status depicted the nurse (210) last entering room (202) two hours ago, and the compliance factor for the "moderately non-compliant") was set to twice the rounding interval, the server may assign a compliance indicator of yellow to room (202) depicted in the automated rounding report. Still further, if the rounding status depicted the nurse last entering room (202) three hours ago and the compliance factor for the "urgent non-compliance"

indicator is set to three times the rounding interval, the server shall assign a compliance indicator of red to room (202) depicted in the automated rounding report. After another ten minutes without visitation, the feedback device might sound an auditory alarm. The server shall regularly perform all of the above processes for a patient shown in the ADT Census database until the patient is discharged and removed from the ADT Census database.

Figure 4:
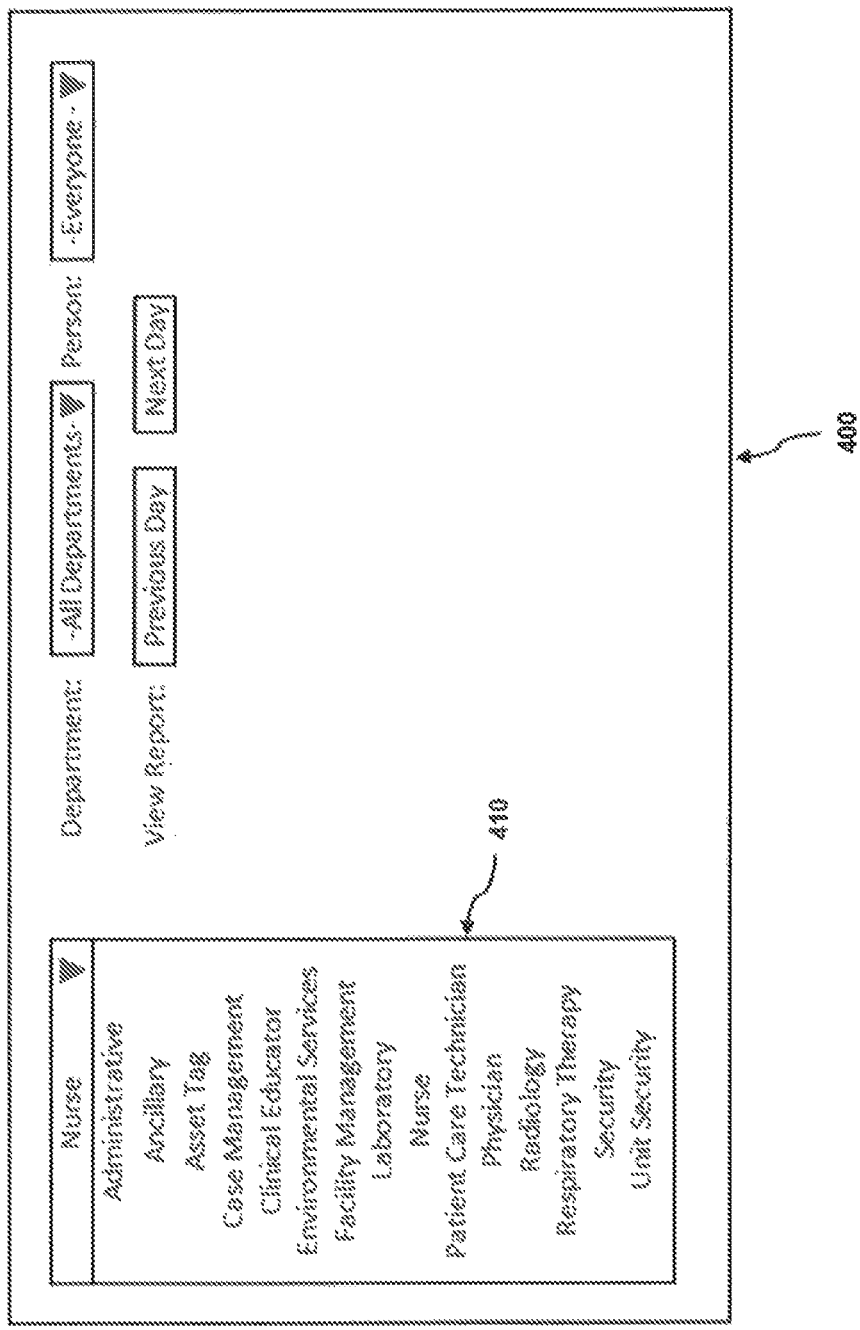
FIG. 4 is an exemplary interface of an embodiment of the present invention for generating rounding reports for a subset of employees based upon data gathered by an HHC system.

Turning to FIG. 4, a user requesting a report of compliance (400) with a hospital procedure can isolate the report of compliance (400) to a class of assets (410). Referring now to FIGS. 1, 2 and 4 collectively, the wearable tag (105) worn by the nurse (210) is operatively classified by the server (125) within the class of assets (410) that is limited to one or more nurses (420). Therefore, once the user has isolated the report of compliance to the class of assets (410) which are of interest, in this instance, the class of assets (410) being limited to one or more nurses (420), the feedback device (230) displays a report of compliance (i.e. rounding report) which is limited to the class of assets (410) pre-selected by the user. However, as demonstrated subsequently in FIG. 5, the user may further isolate the report of compliance (400) for the class of assets (410) to an individual asset (430) encompassed within the class of assets (410).

Figure 5:
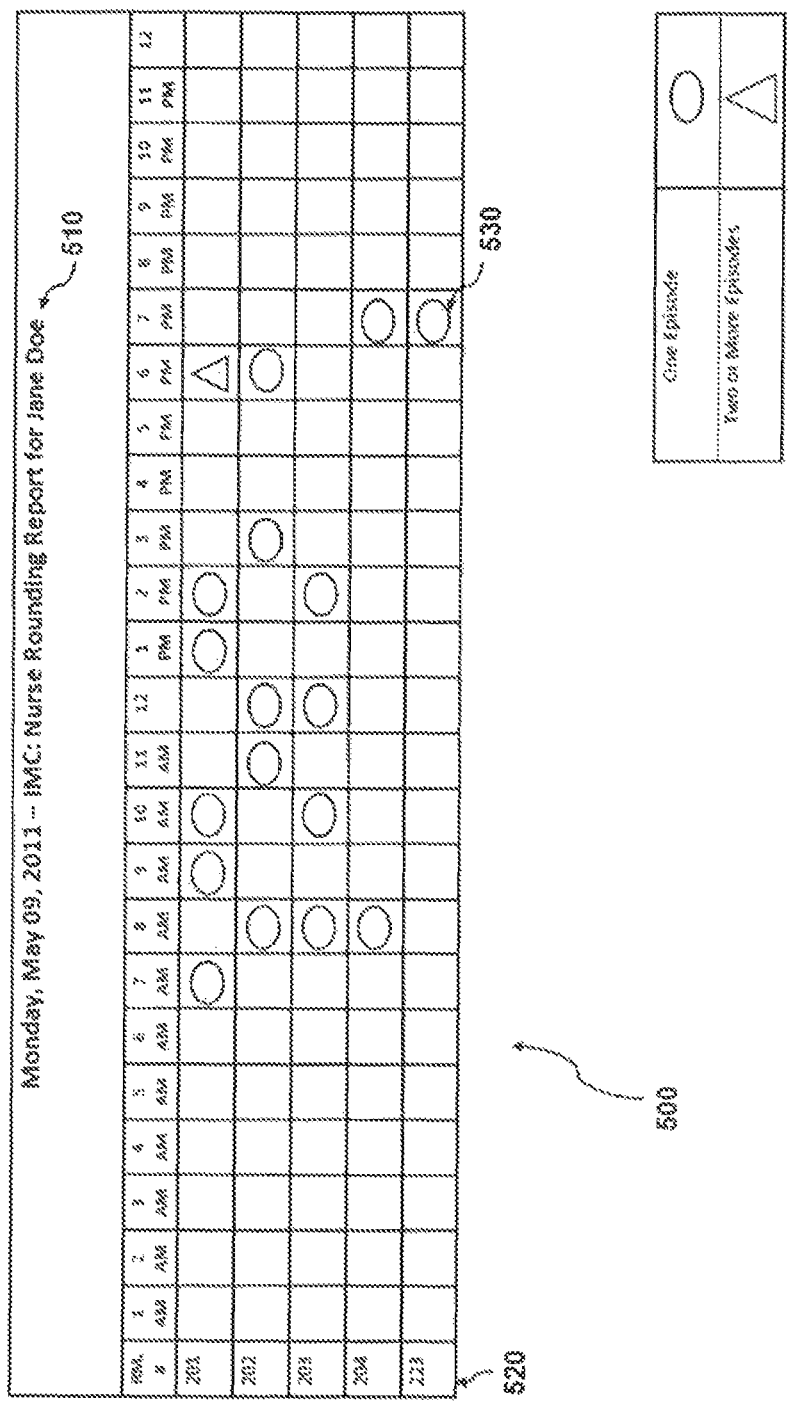
FIG. 5 is an exemplary interface of an embodiment of the present invention for generating rounding reports for an individual employee within a subset of employees from data gathered by an HHC system.

Referring now to FIGS. 1, 4, and 5 collectively, a rounding report (500) is shown for a nurse asset (510) falling within the class of assets (410) limited to one or more nurses (420). The rounding report (500) depicts each of a plurality of rooms (520) where the nurse asset (510) has been in increments of an hour for an entire day. The rounding report (500) has the ability to illustrate a plurality of episodes (530), with the episodes (530) representing instances where the nurse asset (510) was recognized entering a room on multiple occasions by a control unit (115) during any given hour of the day.

Figure 6:
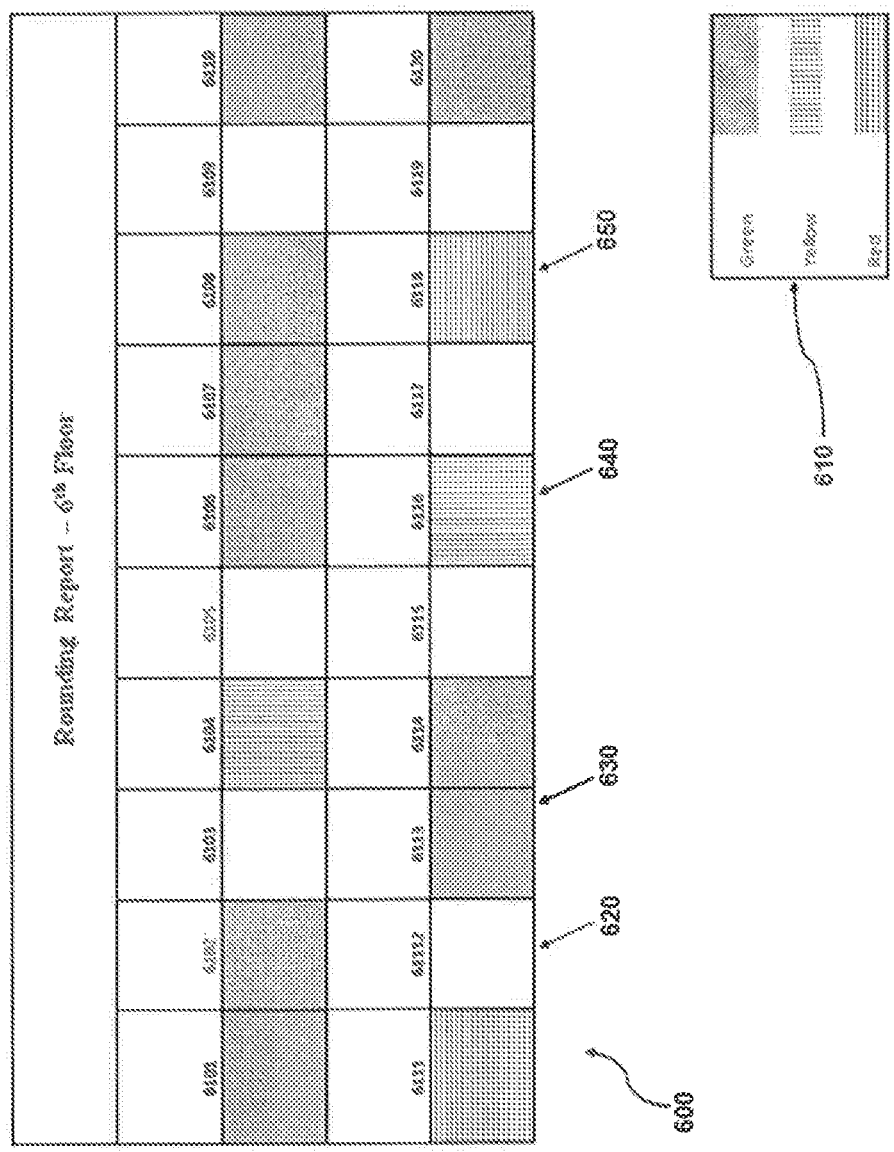
FIG. 6 is an exemplary embodiment of a dynamic rounding report displayed on a feedback device located within a healthcare facility generated by an embodiment of the present invention from data gathered by an HHC system.

FIG. 6 shows an exemplary automated rounding report (600) displayed on a feedback device (230) resulting from data gathered based upon the activities shown in FIG. 2 and the processes of FIG. 3. In one embodiment, the automated rounding report (600) depicts a grid displaying each of a plurality of rooms on a hospital floor equipped with the hand hygiene compliance system. As such, by performing the processes previously discussed in further detail in FIG. 2, the server (125) assigns a compliance indicator to each of the rooms depicted in the automated rounding report (600). In a preferred embodiment, the compliance indicator is a color consisting of green, yellow, red, and white, as indicated by legend (610). in the automated rounding report (600), a room (620) currently unoccupied is assigned the color of white. A room (630) is assigned the color green since the rounding status does not exceed the rounding interval assigned to the room. A room (640) is assigned the color yellow since the rounding status exceeds the rounding interval by a factor of one. A room (650) is assigned the color red since the rounding status exceeds the rounding interval by a factor of two. By assigning a color to each of the rooms depicted in the automated rounding report (600), the server generates a notification regarding compliance with patient rounding in response at least in part to data received front the short-range wireless transmission (160) occurring between the tag radio (140) associated with each of the control units (130) and the wearable tag (105).

Using FIG. 2 as an example to further illustrate the benefit of the automated is rounding report (600) depicted in FIG. 6, the nurse (210) viewing the automated rounding report (600) on a feedback device (230) can readily identify a sequence in which rooms should be visited next to ensure compliance with the rounding interval established by a hospital. In FIG. 6, the room (650) assigned a color of red should be visited first by the nurse (110). Next, the nurse (110) must visit the room (640) assigned a color of yellow. The nurse (110) can go visit the room (630) assigned the color of green. However, the nurse (110) need not expend any time visiting the room (620) assigned a color of white since it is currently unoccupied. In this embodiment, the automated rounding report (600) not only reports existing compliance with hospital procedure, but also directs workflow and aids the nurse in predicting his/her next move using data collected by the hand hygiene compliance system to stay in compliance or remedy non-compliance an efficient manner.

Figure 6A:
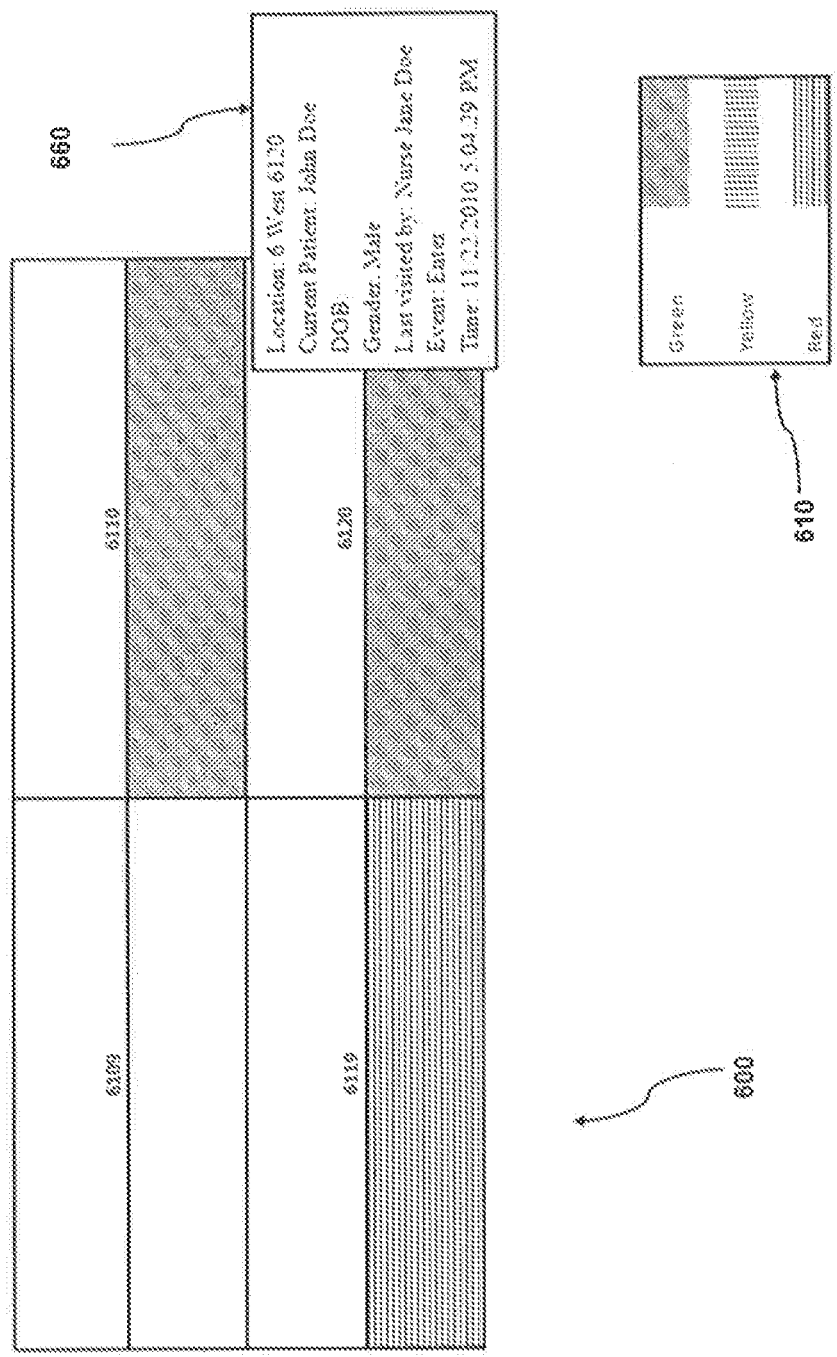
FIG. 6A is an exploded view of the dynamic rounding report depicted in FIG. 5 further illustrating a nurse or doctor's ability to view data relevant to patient rounding.

Turning now to FIG. 6A in conjunction with FIG. 2, an exploded view of an automated rounding report (600) is shown. By using data collected through the short-range wireless transmission (160) occurring between the wearable tag (105) and the tag radio (140) associated with each of the control units (115), a user viewing the automated rounding report (600) may ascertain a rounding status (660) associated with each of the rooms depicted. Using FIG. 2 as an illustrative example, the nurse (210) viewing the automated rounding report (600) on a feedback device (230) located at the nurses' station (220) may view the rounding status (660) associated with an individual patient, As previously stated, the rounding status (660) is comprised of data collected by the control units (115) during the wireless transmission (160) that occurs between the wearable tag (105) and the tag radio (140) associated with each of the control units (115). The rounding status (660) allows a user viewing the automated rounding report (600) to ascertain the time of detection as well as the identity of the wearable tag (105) last seen in each of the rooms depicted in the automated rounding report (600).

In yet another embodiment of the present invention, a control unit may detect the presence a wearable tag (105) associated with a piece of equipment (e.g. a catheter), and in response to movement of the piece of equipment by a wearable tag (105) associated with a person, the server may relay a procedure or a set of is procedures relevant to the piece of equipment and the person on a feedback device associated with the control unit relating to proper administration of the piece of medical equipment and further requiring input by the person through the feedback device confirming compliance with the procedure or the set of procedures.

While an assortment of exemplary embodiments of the present invention have been disclosed for purposes of illustration, it is obvious that many modifications and variations could be made thereto. It is intended to cover all of those modifications and variations which fall within the scope of the present invention, as defined by the following claims.

What is claimed is:

1. A hand hygiene compliance system for use in a facility, the hand hygiene compliance system comprising:
   a plurality of wearable badges, each of the wearable badges associated with an asset;
   a plurality of control units deployed throughout the facility, each of the control units located in proximity to a hand hygiene dispenser and further comprising a sensor to detect use of the hand hygiene dispenser, a first feedback device, a tag radio and a main radio, the first feedback device displaying a touch-screen or touch-free menu of icons upon the sensor detecting use of the hand hygiene dispenser, the tag radio comprising a first antenna to detect, over a first communications channel, a wireless transmission from at least one of the wearable badges each time the at least one of the wearable badges enters an area of the facility in which one of the control units is located and determine, based upon a signal strength indicator associated with the wireless transmission, whether the at least one of the wearable badges is within a predetermined proximity of the control unit located in the area, the main radio in communication with the tag radio and further comprising a second antenna to communicate over a communications network via a second communications channel;

a server in communication with each of the plurality of control units via the communication network, the server operable to receive from the main radio event data relating to the at least one of the wearable badges that the tag radio determines is within the predetermined proximity of the control unit located in the area; and a second feedback device;

wherein the server is operable to perforn at least one of the following actions:
(a) generating a report of compliance with a non-hand hygiene related procedure based at least in part on the event data in response to a query by a user and displaying the report on the second feedback device;
(b) selecting at least one hospital procedure relevant to the event data and providing workflow instructions to a person performing the at least one hospital procedure; or
(c) generating a notification regarding compliance with the non-hand hygiene related procedure in response at least in part to the event data.

2. The system of claim 1, wherein the asset is selected from the group consisting of:
(a) a person;
(b) a piece of equipment; and
(c) a supply.

3. The system of claim 2, wherein the event data includes at least one of the following:
(a) identity of the asset associated with the at least one of the wearable badges detected by the control unit located in the area;
(b) location of the asset;
(c) time of detection of the asset;
(d) movement of the asset; and
(e) the signal strength indicator.

4. The system of claim 3, wherein the action performed is (c) and the non-hand hygiene related procedure is a rounding interval for a patient.

5. The system of claim 4, wherein the notification comprises a rounding report displayed on the second feedback device which is dynamically updated based on the event data received from the control unit located in the area.

6. The system of claim 5, wherein the hand hygiene compliance system accesses hospital census data and the notification excludes from the rounding report any unoccupied room.

7. The system of claim 5, wherein the hand hygiene compliance system accesses a patient information database and assigns the rounding interval, which is specific to individual patients based upon records in the database.

8. The system of claim 5, wherein the second feedback device is a display at a nurses' station.

9. The system of claim 5, wherein the notification directs workflow by identifying a sequence in which patient rooms should be visited to ensure compliance with the non-hand hygiene related procedure.

10. A hand hygiene compliance system for use in a facility, the hand hygiene compliance system comprising:
a plurality of wearable badges, each of the wearable badges associated with an asset;
a plurality of control units, each of the control units located in proximity to a hand hygiene dispenser and further comprising a sensor to detect use of the hand hygiene dispenser, a first feedback device, a tag radio and a main radio, the first feedback device displaying a touch-screen or touch-free menu of icons upon the sensor detecting use of the hand hygiene dispenser, the tag radio comprising a first antenna to detect, over a first communications channel, a wireless transmission from at least one of the wearable badges each time the at least one of the wearable tags enters an area of the facility in which one of the control units is located and determine, based upon a signal strength indicator associated with the wireless transmission, whether the at least one of the wearable badges is within a predetermined proximity of the control unit located in the area, the main radio in communication with the tag radio and further comprising a second antenna to communicate over a communications network via a second communications channel;

a server in communication with each of the control units via the communications network, the server operable to receive from the main radio event data relating to the at least one of the wearable badges that the tag radio determines is within the predetermined proximity of the control unit located in the area; and a second feedback device;

wherein the server is operable to perform at leas the following actions:
(a) generating a rounding report based at least in part upon the event data in order to monitor compliance with a rounding interval assigned to a patient resident at a healthcare facility; and
(b) displaying said rounding report on the second feedback device, wherein the rounding report is dynamically updated in response at least in part to the event data.

11. The system of claim 10, wherein the event data includes at least one of the following:
(a) identity of a person associated with one of the at least one of the wearable badges detected by one of the plurality of control units;
(b) location of the person;
(c) time of detection of the person;
(d) movement of the person; and
(e) the signal strength indicator.

12. The system of claim 10, wherein the hand hygiene compliance system accesses hospital census data and excludes from the rounding report any unoccupied rooms.

13. The system of claim 10, wherein the hand hygiene compliance system accesses a patient information database and assigns the rounding interval to the patient based upon records in the patient information database.

14. The system of claim 10, wherein the second feedback device is a display at a nurses' station.

15. The system of claim 10, wherein there are a plurality of patients, and the rounding report directs workflow by identifying a sequence in which each of the plurality of patients should be visited to ensure compliance with a rounding interval specific to each of the plurality of patients.

16. A hand hygiene compliance system, the hand hygiene compliance system comprising:
a plurality of wearable badges, each of the wearable badges associated with an asset;
a plurality of control units, each of the control units located in proximity to a hand hygiene dispenser and further comprising:
(a) a tag radio comprising a first antenna to detect, over a first communications channel, one or more wireless transmissions from a first wearable badge associated with a piece of medical equipment and a second wearable badge associated with a person and determine, based upon a signal strength indicator associated with each of the one or more wireless transmissions, whether the first wearable badge and the second wearable badge are within a predetermined proximity of the control unit;

(b) a main radio in communication with the tag radio and further comprising a second antenna to send and receive data over a communication network via a second communications channel;

(c) a feedback device to display workflow instructions for performing a procedure responsive to identities of both the piece of equipment and the person once the signal strength indicator associated with at least one of the one or more wireless transmissions from the first wearable badge and second wearable badge indicates both badges are within the predetermined proximity of the control unit; and (d) a sensor to detect use of the hand hygiene dispenser, the feedback device displaying a touch-screen or touch-free menu of icons upon the sensor detecting use of the hand hygiene dispenser.

17. The system of claim 16, wherein the control unit requires input from the person performing the procedure via the feedback device to confirm compliance with the procedure.

18. A method for using a hand hygiene compliance (HHC) system comprising a plurality of wearable badges, a plurality of control units further comprising a first feedback device, and a server to monitor compliance with patient rounding intervals assigned to patients resident at a healthcare facility, the method comprising:

detecting, by a sensor, use of a hand hygiene dispenser, and displaying on the first feedback device of one of the control units, a touch-screen or touch-free menu of icons upon the sensor detecting use of the hand hygiene dispenser;

a first antenna associated with a tag radio of one of the control units detecting, over a first communications channel, a wireless transmission from one of the wearable badges worn by a person, the one of the control units located in proximity to the hand hygiene dispenser and corresponding to a room or area in which a patient of the healthcare facility is resident;

the tag radio determining the person is within a predetermined proximity of the one of the control units based upon a signal strength indicator associated with the wireless transmission;

the tag radio reading an identification code assigned to the one of the wearable badges that identifies the person wearing the one of the wearable badges and is embedded in the wireless transmission;

a second antenna associated with a main radio of the one of the control units transmitting the identification code over a communications network to the server via a second communications channel;

the server, based upon the identification code, identifying the person as being included on a list of authorized personnel;

the server recording a time when the person was within the predetermined proximity of the one of the control units; and the server generating a rounding report to monitor compliance with a rounding interval associated with the patient based upon the recorded time.

19. The method of claim 18, further comprising repeating the identifying and recording steps each time a person included on the list of authorized personnel comes within the predetermined proximity of the one of the control units and updating the rounding report based on the time associated with the most recent iteration of the recording step.

20. The method of claim 19, further comprising displaying the rounding report on a second feedback device wherein the rounding report is updated at least in part each time a person included on the list of authorized personnel comes within the predetermined proximity of the one of the control units.

21. The method of claim 20, further comprising updating the rounding report if no person included on the list of authorized personnel comes within the predetermined proximity for a preselected time period.

22. The method of claim 21, wherein the preselected time period corresponds to a time period selected from the group consisting of: the rounding interval less a specified duration; the rounding interval; and the rounding interval plus a specified duration.

23. The method of claim 22, wherein the second feedback device provides a visual or auditory notification corresponding to each of the preselected time periods.

24. The method of claim 19, further comprising updating the rounding report if no person included on the list of authorized personnel comes within the predetermined proximity for a preselected time period.

* * * * *